(12) United States Patent
Themelis (10) Patent No.: US 11,800,980 B2
(45) Date of Patent: Oct. 31, 2023

(54) AUGMENTED REALITY SURGICAL MICROSCOPE AND MICROSCOPY METHOD

(71) Applicant: LEICA INSTRUMENTS (SINGAPORE) PTE. LTD., Singapore (SG)

(72) Inventor: George Themelis, Lindau (DE)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 1254 days.

(21) Appl. No.: 16/351,733

(22) Filed: Mar. 13, 2019

(65) Prior Publication Data

US 2019/0282099 A1    Sep. 19, 2019

(30) Foreign Application Priority Data

Mar. 16, 2018    (EP) .................................... 18162165

(51) Int. Cl.
*A61B 5/00*    (2006.01)
*A61B 90/20*    (2016.01)
(Continued)

(52) U.S. Cl.
CPC ............ *A61B 5/0071* (2013.01); *A61B 90/20* (2016.02); *A61B 90/36* (2016.02); *A61B 90/37* (2016.02);
(Continued)

(58) Field of Classification Search
CPC ............ A61B 5/0071; A61B 2090/364; A61B 2090/372; A61B 2090/378
See application file for complete search history.

(56) References Cited

U.S. PATENT DOCUMENTS 6,174,291 B1    1/2001  McMahon et al.
2009/0058999 A1*  3/2009  Gono .................... A61B 5/0075
                                                    348/71
(Continued)

FOREIGN PATENT DOCUMENTS

DE    102009000376 A1    8/2010
EP         3205254         8/2017
(Continued)

OTHER PUBLICATIONS

Rouchdy et al., "A Geodesic Voting Method for the Segmentation of Tubular Tree and Centerlines," IEEE International Symposium on Biomedical Imaging: from nano to macro, Mar. 2011, 5 pages.
(Continued)

*Primary Examiner* — Joel F Brutus
(74) *Attorney, Agent, or Firm* — Hodgson Russ LLP (57) ABSTRACT

The invention relates to an augmented reality surgical microscope (1) having a camera (2), preferably a multispectral or hyperspectral camera. The augmented reality surgical microscope (1) retrieves input image data (22) of an object (8) comprising in particular live tissue (10). The input image data (22) comprise visible-light image data (26) as well as fluorescent-light image data (24) of at least one fluorophore (14). The augmented reality surgical microscope (1) permits the automatic identification and marking in pseudo-color (86) of various types of vascular plexus structures (54*a* 54*b*, 54*c*) and/or of blood flow direction (56) depending on the fluorescent-light image data (24). A pre-operative three-dimensional atlas (36) and/or ultrasound image data (39) may be elastically matched to the visible-light image data (26). The augmented reality surgical microscope (1) allows different combinations of the various image data to be output simultaneously to different displays (75). The invention also relates to a microscopy method and a non-transitory com-
(Continued)

puter-readable storing a program causing a computer to execute the microscopy method.

13 Claims, 3 Drawing Sheets
(2 of 3 Drawing Sheet(s) Filed in Color)

(51) Int. Cl.
*A61B 90/00* (2016.01)
*G06F 3/14* (2006.01)
*G06T 11/00* (2006.01)
*G06T 11/60* (2006.01)
*G02B 21/00* (2006.01)
*G06V 20/69* (2022.01)
*G02B 21/16* (2006.01)

(52) U.S. Cl.
CPC ....... *G02B 21/0012* (2013.01); *G06F 3/1423* (2013.01); *G06T 11/001* (2013.01); *G06T 11/60* (2013.01); *G06V 20/693* (2022.01); *A61B 2090/364* (2016.02); *A61B 2090/365* (2016.02); *A61B 2090/372* (2016.02); *A61B 2090/378* (2016.02); *G02B 21/16* (2013.01); *G06T 2210/41* (2013.01); *G06V 2201/03* (2022.01)

(56) References Cited

U.S. PATENT DOCUMENTS

| | | |
|---|---|---|
| 2012/0155735 A1 | 6/2012 | Friedman et al. |
| 2013/0171213 A1 | 7/2013 | Sekine et al. |
| 2014/0371583 A1 | 12/2014 | Flower |
| 2016/0000945 A1 | 1/2016 | Nedergaard et al. |
| 2016/0270656 A1* | 9/2016 | Samec ................. A61M 21/02 |
| 2016/0278678 A1 | 9/2016 | Valdes et al. |
| 2017/0235118 A1 | 8/2017 | Kuster et al. |
| 2017/0236281 A1 | 8/2017 | Dacosta |
| 2017/0258941 A1* | 9/2017 | Tan Hehir .............. A61K 47/32 |

FOREIGN PATENT DOCUMENTS

| | | |
|---|---|---|
| EP | 3248531 | 11/2017 |
| EP | 3284396 | 2/2018 |
| EP | 3410394 | 12/2018 |
| EP | 3422072 | 1/2019 |
| EP | 3505059 A1 | 7/2019 |
| EP | 3514600 A1 | 7/2019 |
| EP | 3527123 A1 | 8/2019 |
| EP | 3530191 A1 | 8/2019 |
| JP | 2013011527 A | 1/2013 |
| JP | 2013092636 A | 5/2013 |
| WO | 2009120228 | 10/2009 |
| WO | 2017204746 A1 | 11/2017 |
| WO | WO-2018002347 A1 * | 1/2018 |

OTHER PUBLICATIONS

Suri et al., "Angiography and Plaque Imaging Advanced Segmentation Techniques," The Biomedical Engineering Series, CRC Press LLC, 2003, pp. 501-530.
"Autofluorescence—Wikipedia," 2018, retrieved from the internet: <https://en.wikipedia.org/wiki/Autofluorescence>.

* cited by examiner

AUGMENTED REALITY SURGICAL MICROSCOPE AND MICROSCOPY METHOD

CROSS REFERENCE TO RELATED APPLICATIONS

This application claims priority of European patent application number 18162165.7 filed Mar. 16, 2018, the entire disclosure of which is incorporated by reference herein.

FIELD OF THE INVENTION

The invention relates to an augmented reality surgical microscope and microscopy method.

BACKGROUND OF THE INVENTION

Current microscopes are able to capture images in different imaging modes, such as white light, fluorescent light of one of more fluorophores and polarized light. However, they are only capable of capturing one mode at a time. During surgery, the surgeon often needs to switch between different imaging modes in order to access all the necessary information. This switching process is cumbersome and distracts the surgeon from surgery. Further, the surgeon essentially needs to combine all the information by memory, which is inevitably inaccurate, prone to mistakes, tiring and requires extensive training and experience.

SUMMARY OF THE INVENTION

It is therefore the object of the invention to provide a microscope device and a microscopy method which facilitate the surgery process and provide the surgeon with all the essential information without distracting from the actual surgery.

According to the invention, this object is solved by an augmented reality surgical microscope comprising an image input system for retrieving input image data, an image processor and an image output system, wherein the input image data comprise subsequent frames of visible-light image data and subsequent frames of fluorescent-light image data of at least one fluorophore, wherein the image processor comprises a pattern recognition module configured to identify at least one vascular plexus structure in at least one of the visible-light image data and the fluorescent-light image data, an image blending module configured to assign at least one pseudo-color to at least one fluorophore and/or to the identified vascular plexus structure in the fluorescent-light image data to generate pseudo-color image data, and to generate output image data including at least one of the visible-light image data, the pseudo-color image data, and any combination of the visible-light image data and the pseudo-color image data, and wherein the image output system is adapted to selectively and simultaneously output different output image data to different output interfaces.

The above object is further achieved according to the invention by a microscopy method for generating output image data of live tissue during surgery, the method comprising the step of acquiring input image data, the input image data comprising subsequent frames of visible-light image data and subsequent frames of fluorescent-light image data of at least one fluorophore, the method further comprising the steps of identifying at least one vascular plexus structure in at least one of the visible-light image data and the fluorescent-light image data, assigning a pseudo-color to at least one of the identified vascular plexus structure and/or to at least one fluorophore in the fluorescent-light image data to generate pseudo-color image data, generating output image data including at least one of the visible-light image data, the pseudo-color image data and any combination of the visible-light image data with the pseudo-color image data, simultaneously outputting different output image data.

The above microscope and microscopy method enable the surgeon to be presented with output images that combine information from a variety of sources, such as visible light and fluorescent light. Additional information is generated by marking vascular plexus structures with pseudo-color. The output image data may be generated from different sources and be selectively accessible at different output interfaces. This allows, for example, the surgical assistant to be presented with different output image data than the surgeon.

The above solution may be further improved by adding one or more of the following features, which can be combined independently of one another and of which each has a distinctive technical effect. Each of the following features may be added indiscriminately to the microscope or to the microscopy method.

For example, the image acquisition system does not necessarily include a camera but may comprise one or more input interfaces which are adapted to input image data into the microscope.

Preferably, the intensity distribution is homogenized at least in the fluorescent-light image data. This may e.g. be done in a homogenization module of the image processor. In the homogenized fluorescent-light image data, an uneven distribution of illumination in the at least one fluorescence triggering spectrum may be compensated for. Such a compensation may be determined by e.g. measuring the intensity distribution on a sample of uniform color and brightness, such as a gray card, and using the measured distribution for inverse filtering.

The microscope may comprise an image storage system, in which any type of image data described herein may be stored at least temporarily. The image storage system may comprise volatile and/or non-volatile memory and be removably or stationarily mounted.

If a plurality of fluorophores having different, preferably non-overlapping fluorescence emission spectra is used, the fluorescent-light image data may comprise a plurality of different sets of fluorescence-band image data. Each set is assigned a different spectral band. Each set of fluorescence-band image data may comprise subsequent frames. If reference is made to the fluorescent-light image data, this may relate to a single set of fluorescence-band image data or to more than one set of fluorescence-band image data.

For the simultaneous acquisition of a plurality of different sets fluorescence-band image data, at least one multispectral or hyperspectral camera may be included in the microscope. Each fluorescence emission band, preferably also including auto-fluorescence bands, of a fluorophore is preferably mapped onto at least one of the different spectral bands of the multispectral or hyperspectral camera.

Each of the different sets fluorescence-band image data may be homogenized independently of the other sets of fluorescence-band image data. In each of the sets of fluorescence-band image data, a vascular plexus structure may be identified independently of the other sets of fluorescence-band image data. Any of the sets of fluorescence-band image data and any of the vascular plexus structures may be assigned a different pseudo-color, so that a plurality of sets of pseudo-color image data is generated. The different sets of pseudo-color image data may each by itself or in any combination with one another and/or the visible-light image data be output as output image data. Also, the fluorescent-light image data, each set of fluorescence-band image data and the visible-light image data may also be directly output as output image data without being combined with other image data.

One set of fluorescence-band image data may be used to automatically determine a blood flow direction, whereas another set of fluorescence-band image data or a plurality of different sets of fluorescence-band image data may be used to automatically determine a vascular plexus structure.

In another embodiment, the image processor may be further adapted to automatically identify a preferably pre-determined type of vascular plexus structure depending on a change of fluorescence intensity at a particular location in subsequent frames of the fluorescent-light image data or the homogenized fluorescent-light image data, or at least one set of the fluorescence-band image data and to automatically assign a pseudo-color to the identified vascular plexus structure depending on the type of the identified vascular plexus structure. The image data, in which the type of structure is marked with a pseudo-color form a set of pseudo-color image data, which may be used as output image data or combined with the visible-light image data and/or any other type of pseudo-color image data. The type of the vascular plexus structure may, for example, be one of an arterial vascular plexus structure, a venous vascular plexus structure and a capillary vascular plexus structure. Each of these types may be assigned a different pseudo-color, e.g. blur for the venous vascular plexus structure, red for the arterial vascular plexus structures and yellow or green for the capillary vascular plexus structures. Each of these types may be assigned to different pseudo-color image data to allow independent image processing of the different types. A device and method for a classification of tissue is disclosed in European patent application EP 17 17 40 47.5, which is herewith enclosed in its entirety by reference.

For the morphological identification of a vascular plexus structure, an algorithm as e.g. disclosed in Suri, S., Laxmi-narayan, S. (2003): "Angiography and Plaque Imaging: Advanced Segmentation Techniques", CRC-Press, pp. 501-518; Rouchdy, Y., Cohen, L. (2011): "A geodesic voting method for the segmentation of tubular tree and centerlines", IEEE Symposium on Biomedical Imaging, DOI 10.1109/ISBI.2011.5872566, pp. 979-983 may be used. Further, subsequent frames of fluorescent-light image data may be used to automatically determine blood flow direction in a morphologically identified vascular plexus structure. A microscope and microscopy method for automatically determining and displaying blood flow direction in a morphologically identified vascular plexus structure is described in European patent application EP 17 21 09 09.2, which is herewith enclosed in its entirety by reference. As disclosed in this application, the blood flow direction in the identified vascular plexus structure may be automatically determined in real time using at least one of a spatial gradient of fluorescence intensity along the identified vascular plexus structure and a temporal gradient at the same location of the identified vascular plexus structure across subsequent frames of at least one of the fluorescent-light and/or fluorescence-band image data and homogenized fluorescent-light and/or fluorescence-band image data. At least part of the identified morphological structure of the vascular plexus structure may be replaced by or blended with a time-varying and/or spatially varying pseudo-color pattern which differs depending on the blood flow direction. The pattern recognition module may be configured to automatically identify a vascular plexus structure morphologically and to generate a set of pseudo-color image data, in which at least part of the identified morphological structure of the vascular plexus structure is replaced by or blended with a time-varying and/or spatially varying pseudo-color pattern which differs depending on the blood flow direction.

In another embodiment of the invention, the input image data may comprise a two- or three-dimensional atlas of pre-operative image data. Such an atlas may be generated by e.g. MRT. Additionally or alternatively, a two- or three-dimensional atlas may be generated as ultrasound image data by a medical ultrasound system. The ultrasound image data may be generated during surgery or pre-operatively.

The atlas may be elastically mapped to at least one of the visible-light image data and the fluorescent-light image data, using e.g. the system and method described in European patent application EP 18 15 69 06.2, which is herewith enclosed in its entirety by reference.

The elastic matching module is preferably adapted to elastically match at least one of the fluorescent-light image data, the homogenized fluorescent-light image data, at least one set of the pseudo-color image data, the ultrasound image data and the pre-operative image data to the visible-light image data.

An elastically matched subset of the three-dimensional atlas may be combined with at least one of the fluorescent-light image data, including any of the sets of fluorescent-band image data contained therein, the homogenized fluorescent-light image data, the pseudo-color image data, the ultrasound image data and the visible-light image data in at least one set of output image data, which may be selectively transmitted to at least one output interface. Using the elastically matched subset, live tissue structures located beneath the visible surface of the object under investigation can be made visible in the output image data.

For combining any of the image data with pseudo-color, the blending process and device described in European patent application EP 16 15 56 25.3, which is herewith enclosed in its entirety by reference, may be used.

The augmented reality surgical microscope may comprise a plurality of output devices, such as at least one of stereoscopic displays, a two-dimensional and/or three-dimensional display, augmented reality goggles, a projector and storage or memory systems. For each different output device, a separate output interface may be provided, each interface being adapted to receive different output image data.

Finally, the invention relates also to a non-transitory computer-readable medium storing a program, causing a computer to execute the image processing method in any of the configurations described in this specification.

In the following, the invention is described in detail with reference to the opening drawing, using an exemplary embodiment. The specific combination of features shown in this embodiment is for explanatory purposes only and may be altered according to the above description of the various additional features. For example, a feature may be omitted if its technical effect is not needed in a particular application and vice versa: a feature may be added if, for a particular application, its technical effect is needed.

BRIEF DESCRIPTION OF THE DRAWING VIEWS

The patent or application file contains at least one drawing executed in color. Copies of this patent or patent application publication with color drawing(s) will be provided by the Office upon request and payment of the necessary fee.

In the drawings, identical reference numerals are used for elements that correspond to each other with respect to at least one of function and design.

In the drawings.

DETAILED DESCRIPTION OF THE INVENTION

In the following, the invention is described with reference to FIGS. 1, 2 and 3.

Figure 1:
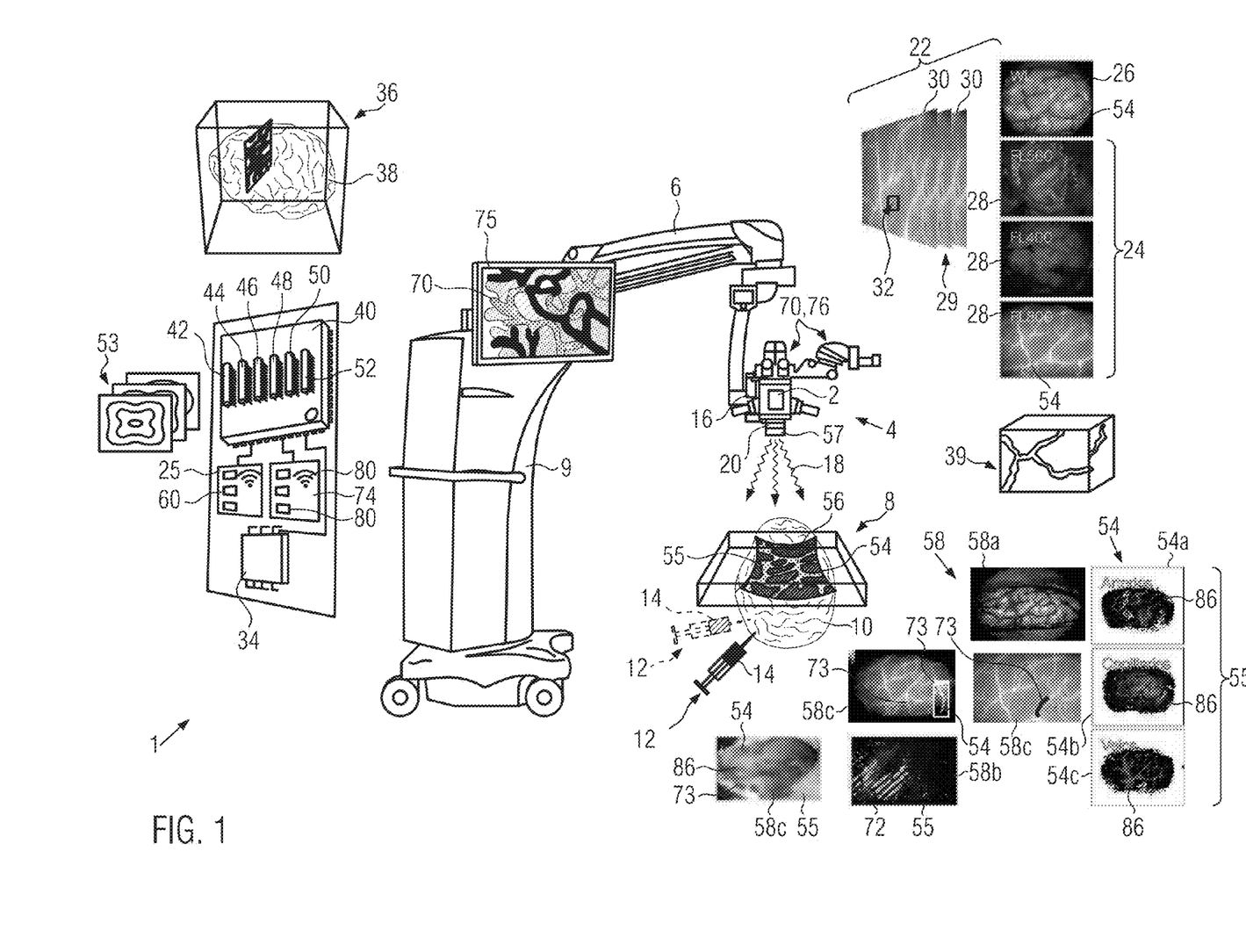
FIG. 1 shows a schematic representation of an augmented reality surgical microscope according to the invention.

FIG. 1 shows an augmented reality surgical microscope 1. The microscope 1 is provided with at least one camera 2, which preferably comprises at least one multispectral or hyperspectral camera. The camera 2 is located in an optics holder 4 which is mounted on a movable cantilevered and/or telescopic arm 6 to be positioned freely above an object 8 to be observed during surgery. The arm 6 is supported on a frame 9 of the microscope 1, which may be stationary or which may be moved on wheels.

Typically, the object 8 comprises live tissue 10 which may have been provided with at least one bolus 12 of at least one fluorophore 14. The surgical microscope 1 may also comprise an illumination system 16, which may also be arranged within the optics holder 4. Illumination light 18 from the illumination system 16 may be guided through a microscope lens 20 onto the live tissue 10. The camera may also use the microscope lens 20.

If the live tissue 10 comprises at least one bolus 12 of one or more fluorophores 14, and if the illumination light 18, or the ambient light, comprises wavelengths in which the fluorescence of the respective fluorophores 14 is triggered, the camera 2 may acquire input image data 22 comprising fluorescent-light image data 24, i.e. data which represent an image of the live tissue recorded at the fluorescence emission wavelengths of the at least one fluorophore.

If no fluorophore is contained in the live tissue 10, the input image data 22 may solely comprise visible-light image data 26 of the live tissue 10. Alternatively or in addition to the fluorescence of a fluorophore 14, the camera 2 may also be configured to detect auto-fluorescence of the live tissue 10 or the fluorophore 14 which may be triggered by the illumination light 18 or the fluorescence of the fluorophore 14.

If the camera 2 is a multispectral or hyperspectral camera, each fluorescence waveband of a fluorophore 14 and/or of auto-fluorescence may be mapped onto a different array of sensors, i.e. a different spectral band, of the multispectral and hyperspectral camera. The fluorescent-light image data 24 may thus comprise one or more sets of fluorescence-band image data 28, each representing an image of the object 8 at a different fluorescence spectrum. A fluorescence spectrum corresponds to a limited, often narrow, spectral band preferably centered about the fluorescence emission spectrum of the fluorophore 14 or a pre-determined type of tissue or substance in the live tissue 10. Three sets of fluorescence-band image data 28 are shown in FIG. 1 only for exemplary purposes, one being generated by a fluorophore 14 having a fluorescence emission spectrum centered at a wavelength of 570 nm (FL 570), by another fluorophore 14 having a fluorescence emission spectrum centered at a wavelength of 400 nm (FL 400), and another fluorophore 14 having a fluorescence emission spectrum centered at a wavelength of 800 nm (FL 800).

The advantage of using a multispectral or hyperspectral camera is that in addition and simultaneously to the fluorescent-light image data 24, the visible-light image data 26 (WL in FIG. 1) may be recorded using at least three different spectral bands for representing the visible light.

The input image data 22 in at least one of the fluorescent-light image data 24, visible-light image data 26 and fluorescence-band image data 28 preferably comprises or consists of a time series 29 of subsequent frames 30, each frame in turn comprising a plurality of pixels 32.

The image data 22, 24, 26 and 28 may be stored in an image storage system 34, which may be a volatile or non-volatile memory, such as RAM, ROM, a disk drive or a memory card such as an SD or micro-SD card. The storage system 34 may be stationary with the microscope 1 or be configured to be repeatedly insertable into and removable from the microscope 1. Any other type of storage from which the image data 22, 24, 26, 28 may be retrieved is deemed to be comprised by the term 'image storage system'.

The image storage system 34 may also comprise a three-dimensional atlas 36 of pre-operative image data 38. The pre-operative image data 38 may have been obtained from the object 8, for example by MRT, prior to observation by the microscope 1. The input image data 22 may comprise the pre-operative image data 38.

The input image data 22 may also comprise image data from other sources, such as two- or three-dimensional ultrasound image data 39, which were generated by an imaging ultrasound system such as the one disclosed in European patent application EP 18 15 88 58.3 which is herewith incorporated in its entirety by reference.

The augmented reality surgical microscope 1 may further comprise an image processor 40, which is adapted to work on any of the input image data 22, 24, 26, 28 and 38. The image processor 40 may be made from software, hardware or a combination of both. For example, the image processor may comprise a general-purpose computer, or a processor such as a CPU and/or GPU with memory, or a special-purpose IC, such as an ASIC.

Figure 2:
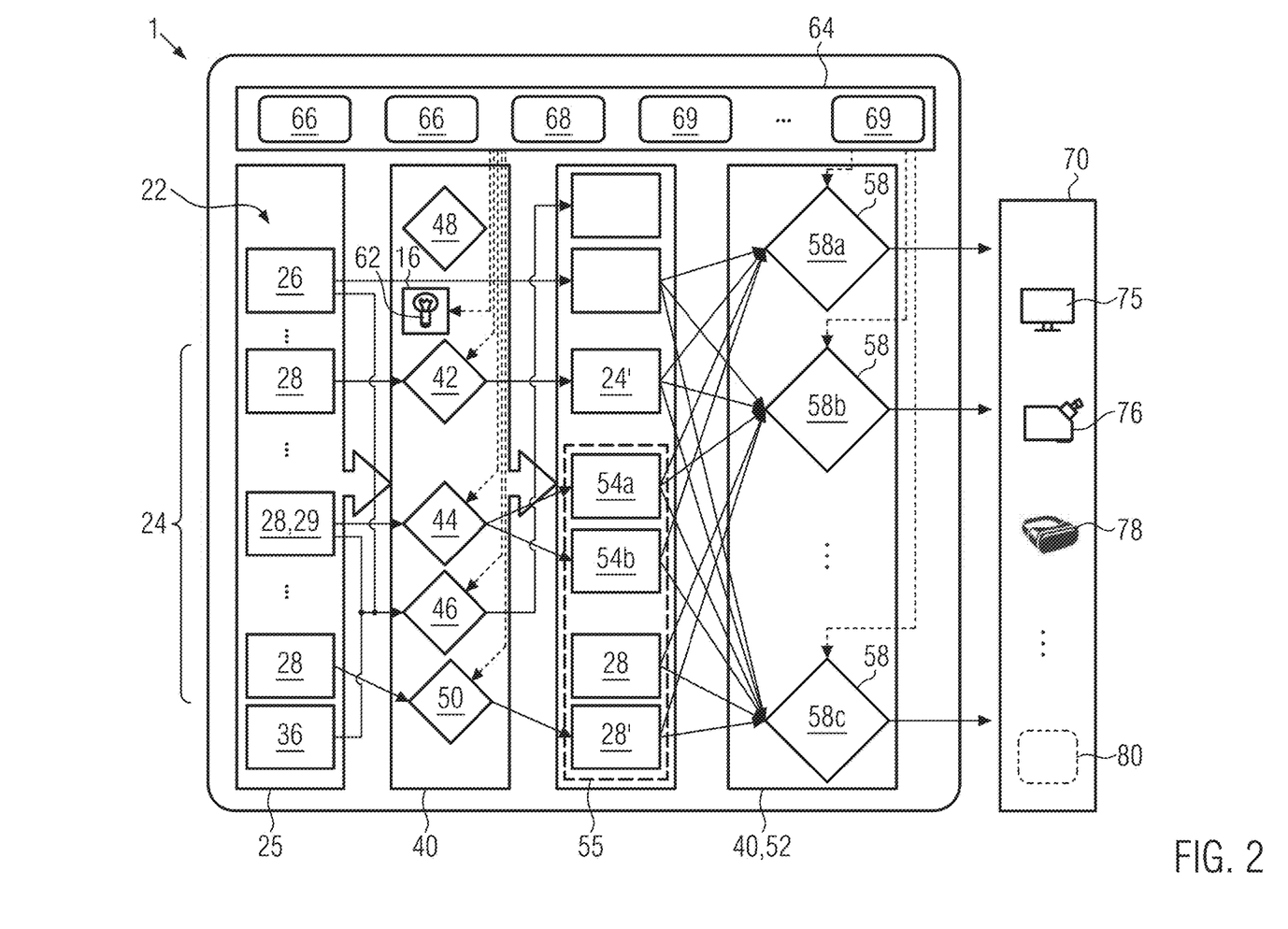
FIG. 2 shows a schematic representation of a microscopy method according to the invention.
Figure 3:
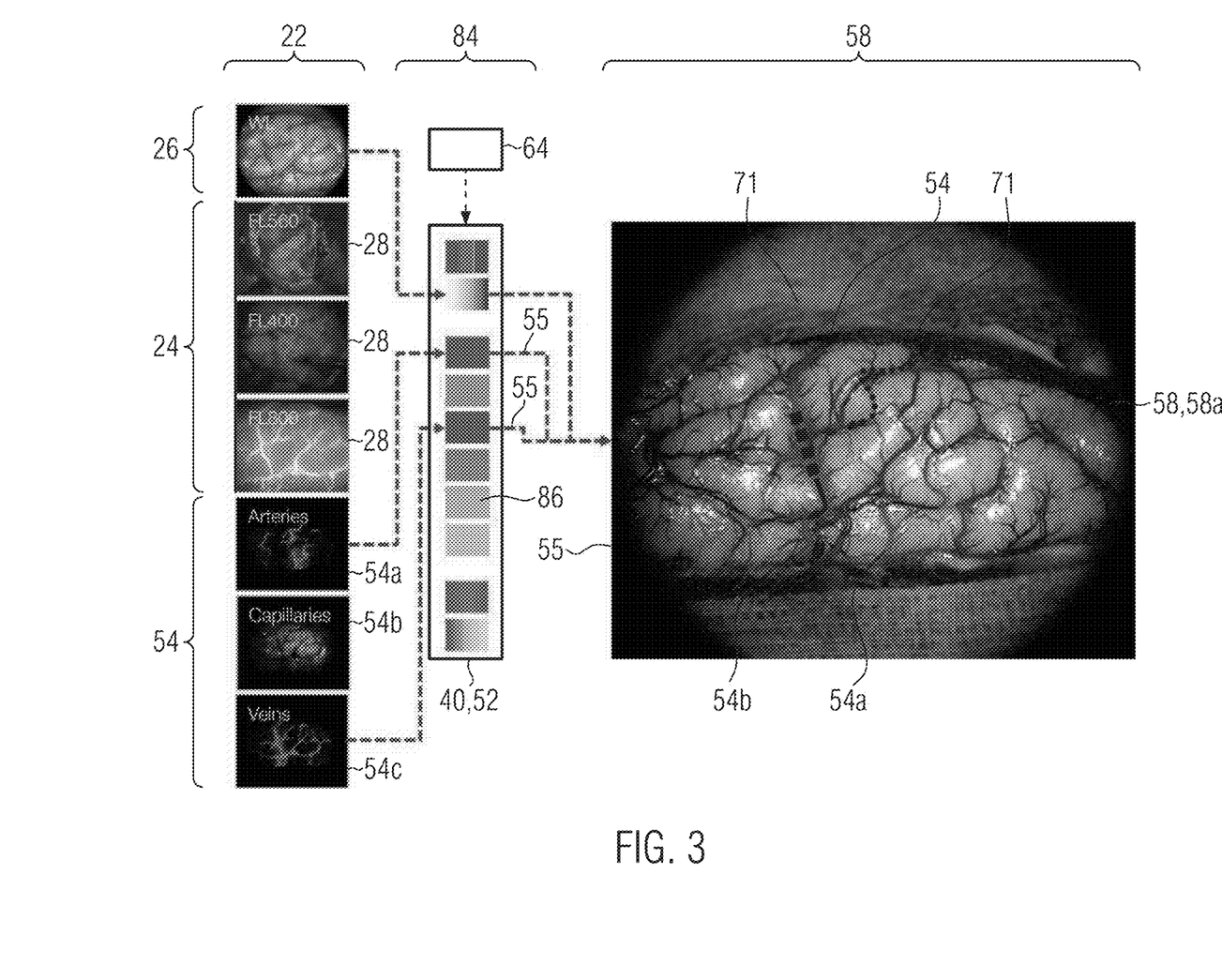
FIG. 3 shows sample images obtained by the augmented reality surgical microscope according to the invention and the microscopy method according to the invention.

For example, with reference also to FIG. 2, the image processor 40 may comprise a homogenization module 42, a kinetics analysis module 44, an elastic matching module 46, a pattern recognition module 48, a spectral unmixing module 50 and a image blending module 52. The modules 42 to 52 may again be implemented in software, hardware or a combination of both.

The homogenization module 42 is adapted to homogenize the intensity distribution across a frame 30 of the fluorescent-light image data 24 or independently any set of the fluorescence-band image data 28. As the result of the homogenization, homogenized fluorescent-light image data 24 are obtained, which may comprise one or more sets of homogenized fluorescence-band image data 28.

For the homogenization, the augmented reality surgical microscope 1 may comprise a stored homogenization function 53 which may e.g. be obtained by having, as an object 8, a uniform object 8 which is illuminated by the fluorescence excitation wavebands of the illumination light 18. Each fluorescence band preferably has its own homogenization function 53. The uniform object 8 may also comprise geometric patterns to record optical distortions. From this, the homogenization function 53 may be derived as the inverse of the illumination distribution and/or the distortion. Of course, the visible-light image data 26 may also be homogenized, e.g. by the same module and/or method as the fluorescent-light image data 24. With regard to the homogenization, reference is made to European patent application EP 18 15 26 17.9, which is herewith incorporated by reference in its entirety.

The kinetics analysis module 44 is adapted to process a time series 29 of frames 30. The kinetics analysis module 44 is configured to classify at least one type of vascular plexus structure 54 in the live tissue 10 and/or to identify the blood flow direction 56 based on the fluorescent-light image data 24 or the homogenized fluorescent-light image data 24.

The kinetics analysis module 44 is preferably adapted to retrieve and process subsequent frames 30 of fluorescent-light image data 24. By, for example, performing a principal component analysis on the time-development of the bolus 12 at a particular location 57 in the live tissue 10, the type of vascular plexus structure 54 may be automatically determined to be, for example, one of an arterial vascular plexus structure 54a, a venous vascular plexus structure 54b and a capillary vascular plexus structure 54c. In the microscope 1, the different identified vascular plexus structures 54a, 54b, 54c may be each represented by pseudo-color image data 55 in which each of the structures 54a, 54b, 54c may be automatically assigned a different pseudo-color. For each different type of vascular plexus structure 54a, 54b, 54c, a different set of pseudo-color image data 55 may be provided to allow independent processing of the different vascular plexus structures 54a. 54b, 54c.

The automatic identification of the type of vascular plexus structure based on the time-development of a bolus 12 of the at least one fluorophore 14 is described in European patent application EP 17 17 40 47.5, which is herewith incorporated in its entirety by reference.

The kinetics analysis module 44 may also be used to determine the blood flow direction 56 in the fluorescent-light image data 24, in particular in a vascular plexus structure 54 which has previously been identified morphologically by the pattern recognition module 48. The morphological identification of a vascular plexus structure differs from the classification of its type in that in the morphological identification the geometric extent of a contiguous vascular plexus structure in the image data is determined without classifying its type.

The morphological identification of a vascular plexus structure 54 is described e.g. in Suri, S., Laxminarayan, S. (2003): "Angiography and Plaque Imaging: Advanced Segmentation Techniques", CRC-Press, pp. 501-518; Rouchdy, Y., Cohen, L. (2011): "A geodesic voting method for the segmentation of tubular tree and centerlines", IEEE Symposium on Biomedical Imaging, DOI 10.1109/ISBI.2011.5972576, pp. 979-983. Using the device and method described in European patent application EP 17 21 09 09.2, which is herewith incorporated in its entirety by reference, the blood flow direction 56 may be determined in a morphologically identified vascular plexus structure 54 using the temporal derivative at a given location 57 within the identified vascular plexus structure 54 over subsequent frames 30 of the fluorescent-light image data 24 and, in another embodiment, additionally the spatial derivative along the identified vascular plexus structure 54. Another set of pseudo-color image data 55 may be generated by assigning to the morphologically identified vascular plexus structure 54 a time-varying and/or spatially varying pseudo-color pattern. Preferably, the pattern depends on at least one of the blood flow direction 56 or the blood flow velocity.

Another set of pseudo-color image data 55 may be generated from the ultrasound image data 39 by assigning a time-varying and/or spatially varying pseudo-color pattern depending on at least one of the blood flow direction 56, the blood flow velocity and blood flow rate. The kinetics analysis module 44 may be adapted to perform such an assignment prior or after elastically matching the ultrasound image data 39 to the visible-light image data 26.

The elastic matching module 46 is adapted to match the vascular plexus structure 54 which has been identified by the pattern recognition module 48 in a time series of frames 30 of fluorescent-light image data 24 to subsequent frames and/or to other image data. Thus, the location 57 and its properties, such as blood flow direction 56, may be tracked in the time series of frames 30. The pattern recognition module 48 may also be adapted to elastically match the pre-operative three-dimensional atlas 36 to the visible-light image data 26.

The method that may be employed for elastic matching is e.g. described in European patent application EP 18 15 69 06.2, which is herewith incorporated by reference in its entirety. Further, the pattern recognition module 48 may be adapted to elastically match any type or subset of input image data 22 to another subset of input image data 22. If, for example, the input image data 22 correspond to ultrasound image data 39 that have been generated by an imaging ultrasound device, the ultrasound image data 39 may be elastically matched to the visible-light image data 26 or the fluorescent-light image data 24.

The spectral unmixing module 50 is adapted to extract different fluorescence spectra from the input image data 22, in particular from a single set of fluorescence-band image data 28. The spectral unmixing module 50 may also comprise an optical filter arrangement 58, e.g. one or more narrow bandpass filters where the passband is preferably limited to the respective fluorescence emission spectrum of the fluorophore 14. The filter arrangement 58 reduces cross-talk between different fluorescence spectra.

The spectral unmixing module 50 may further be adapted to separate auto-fluorescence image data 28', e.g. of tissue, digitally from the fluorescence-band image data 28. Auto-fluorescence may result as an unwanted or unintended effect when fluorescence in the tissue 10 is triggered by the illumination light 18 or is triggered by the excited fluorescence as a secondary effect. Examples of a spectral unmixing module 50 and the filter arrangement 58 are contained in European patent application EP 17 17 90 19.9, which is herewith incorporated in its entirety by reference. If a multispectral and/or a hyperspectral camera is used, and the fluorescence spectra in which auto-fluorescence will occur, are known, it is preferred that different auto-fluorescence spectra are assigned to different spectral bands of the camera. These spectral bands are preferably different from the spectral bands of the camera, in which the triggered fluorescence is recorded. If no such separation of the spectral bands occurs in the camera, the spectral unmixing module 50 may comprise at least one digital bandpass filter, of which the passband is matched to an auto-fluorescence spectrum. The digital bandpass filter may be an IIR or FIR filter. Preferably, for each auto-fluorescence spectrum, there is a matching digital bandpass filter.

The image blending module 52 is adapted to blend any of the image data in the microscope 1 with a pseudo-color to generate pseudo-color image data 55, another one of the input image data 22 and/or the processed image data 24', 28', 54a, 54b, 54c. The structure and method implemented by the image blending module 52 is described in European patent application EP 16 15 56 25.3, which is also incorporated herewith in its entirety by reference.

For example, a location 57 within an identified type of identified vascular plexus structure 54a, 54b, 54c may be automatically assigned a pseudo-color in the output image data 59. The pseudo-color is located linearly in a color space between the color of the location 57 i.e. visible-light image data 26 and a pseudo-color. The location 57 may correspond to one pixel or a set of pixels in the respective frame 30. In particular, the distance in color space of the color of the corresponding location 57 in the output image data 59 and the pseudo-color may be proportional to the intensity at this location in the fluorescent-light image data 24, or any subset thereof, respectively.

The image blending module 52 may generate at least one set of output image data 59 from any combination of the image data 24, 24', 26, 28, 28', 36, 54a, 54b, 54c, 55, or from just one set of these image data alone.

Each of modules 42 to 52 may be implemented as hardware, as software, or a combination of both. For example, a module may be realized as one or more subroutines in a computer program, as a section of a CPU and/or as an ASIC.

As is further seen in FIG. 1, the augmented reality surgical microscope 1 may comprise a plurality of input interfaces 60 which are configured to be connected to a variety of devices for providing input image data 22. The input interfaces 60 may be standardized wire-based protocols, sockets or connectors, such as TCP/IP, DVI, HDMI, USB and/or wireless connections, such as WiFi, to receive at least one set of the input image data. The input interfaces 60 are part of the image input system 25. In particular, the input image data 22 need not, as exemplified by the three-dimensional atlas 36 or the ultrasound image data 39, be generated by optical means but may also be generated using X-rays, MRT, ultrasound and/or PET. For example, the combined camera/ultrasound-head as described in European patent application EP 18 15 88 58.3, which is herewith incorporated by reference in its entirety, may be connected to the microscope 1, may be part of the microscope 1. Input image data 22 may be acquired also or solely from this ultrasound head.

The illumination system 16 may comprise a light source 62, which has an adjustable spectrum. In particular, the illumination spectrum of the at least one light source 62 may be adapted automatically to the reflectance of the object 8 and/or the fluorescence excitation spectrum of the at least one fluorophore 14, as described in European patent application EP 16 18 43 11.5, which is herewith incorporated by reference in its entirety.

The operation of the modules 42 to 52 may be controlled by a customization section 64. The customization section 64 may comprise sensors 66 which automatically acquire operational parameters 68 of the microscope 1, such as at least one of the focal length of the microscope lens 20, the distance setting of the microscope lens 20, the brightness of the input image data 22, the average spectrum of the input image data 22, the illumination spectrum of the illumination system 16, amongst others. Further, the customization section 64 may comprise user settings 69 that can be adjusted manually before and/or during operation of the microscope 1. For each of the different output devices 70, different user settings 69 may be stored in the customization section 64. For example, the image blending module 52 may blend into the output image data 59 only those input image data 22 or processed image data 24', 28', 54a, 54b, 54c, 55 which have been manually selected for blending in the customization section 64. Various possibilities for combining the input image data 22 are indicated by the arrows 71 in FIG. 2. For example, in output image data 59a, the visible-light image data 22, the set of pseudo-color image data 55 from the homogenized fluorescent-light image data 24' and the sets of pseudo-color image data 55 of the different types of vascular plexus structures 54a, 54b, 54c, each type in a different pseudo-color, may be blended with one another.

In another set of output image data 59b, preferably homogenized fluorescence-band image data 28 may be blended, wherein each fluorescence band is assigned a different pseudo-color and/or spatially varying pattern 72, the brightness of the pseudo-color and/or spatial pattern depending e.g. on the fluorescence intensity of that location 57.

Another set of output image data 59c may comprise a time-varying pattern 73 generated by the image processor 40. The time-varying pattern 73 may be restricted to and/or at least partly cover an identified vascular plexus structure 54 and/or its appearance in subsequent output image data 59c may be dependent on at least one of blood flow direction 56 and blood flow velocity. The time-varying pattern 73 may, for example, be an arrow which changes size and direction depending on blood flow velocity and blood flow direction 56, or a progress bar in which a pattern is contained that advances in the blood flow direction 56 over subsequent frames 30 of the output image data 59c. The appearance of the time-varying marker may be defined in the user settings 69. The generation of a time-dependent marker is described in European patent application EP 16 17 07 69.0, which is herewith incorporated in its entirety by reference.

Of course, any other combination of input image data 22 or image data 24', 28' 54a, 54b, 54c may be blended in the output image data 59. Any number of different output image data 59 may be output simultaneously. It is to be noted in this context that separate pseudo-color image data 55 need not to be generated prior to their blending into the output image data 59. Instead, the pseudo-color and the respective image data 22 may be blended on the fly into the output image data 59 without a complete set of separate pseudo-color image data 55 being generated.

However, for computational purposes, if for example the same pseudo-color image data 55 need to be blended into two different sets of output image data 59, it may be more efficient to generate the pseudo-color image data 55 once and store them temporarily than to compute them anew for each set of output image data 59.

For outputting the output image data 59, the augmented reality surgical microscope 1 further comprises an image output system 74 which is adapted to be connected to a variety of output devices 70. Preferably, the output devices 70 comprise one or more different displays 75, such as at least one three-dimensional and/or two-dimensional display 75, at least one stereoscopic display 76, augmented reality goggles 78 and others 80, e.g. a projector, or an image recording and/or storage system. In particular, depending on the operational parameters 68 in the customization section 64, different output image data 59 may be provided simultaneously at different output interfaces 82 of the image output system 74. For example, the surgeon at the stereoscopic display 76 may be provided with different output image data 59 than the assistant who observes the display 75. If the surgeon uses augmented reality goggles 78, they may also again be provided with different output image data 59 simultaneously with the output image data 59 for the other output devices 70. The output interfaces 82 may comprise standardized protocols, connectors and sockets, such as TCP/IP, HDMI, DVI and USB, or wireless connections, such as WiFi, for outputting the output image data 59 to the output devices.

The input interface 60 and/or the image output system 74 may comprise any combination and number of preferably standardized hardware connectors and/or wireless connections.

The augmented reality surgical microscope 1, in particular the image blending module 52, may further comprise a color palette 84 (FIG. 3) which may be stored in the image storage system 34 or any other storage system of the microscope 1. Depending on the user settings 69 in the customization section 64, and/or depending on the type of vascular plexus structure 54 and/or the blood flow direction 56 as identified by the kinetics analysis module 44, the augmented reality surgical microscope 1 may automatically assign different pseudo-colors 86 of the color palette 84 to different locations 57 in the output image data 59. The visible-light image data 26 and/or the fluorescent-light image data 24 as described above may preferably be displayed as color images or as grayscale images in the output image data 59.

The augmented reality surgical microscope 1 operates in real time. Thus, all the above output image data 59 are provided to the surgeon in real time.

REFERENCE NUMERALS 1 augmented reality surgical microscope
2 camera
4 optics holder
6 cantilevered arm
8 object
9 frame
10 live tissue
12 bolus
14 fluorophore
16 illumination system
18 illumination light
20 microscope lens
22 input image data
24 fluorescent-light image data
24' homogenized fluorescent-light image data
25 image input system
26 visible-light image data
28 fluorescence-band image data
28' auto-fluorescence image data
29 time series
30 frames
32 pixels
34 image storage system
36 three-dimensional atlas
38 pre-operative image data
39 ultrasound image data
40 image processor
42 homogenization module
44 kinetics analysis module
46 elastic matching module
48 pattern recognition module
50 spectral unmixing module
52 image blending module
53 homogenization function
54 vascular plexus structure
54a arterial vascular plexus structure
54b venous vascular plexus structure
54c capillary vascular plexus structure
55 pseudo-color image data
56 blood flow direction
57 location in object or live tissue
58 filter
58a filter
58b filter
58c filter
59 output image data
59a example of output image data
59b example of output image data
59c example of output image data
60 input interface
62 light source
64 customization section
66 sensor
68 operational parameters
69 user settings
70 output devices
71 arrows
72 spatially varying pattern
73 time-varying pattern
74 image output system
75 display
76 stereoscopic display
78 augmented reality goggles
82 output interface
84 color palette
86 pseudo-color

What is claimed is:

1. An augmented reality surgical microscope comprising:
an image input system for retrieving input image data;
an image processor; and
an image output system having different output interfaces;
wherein the input image data comprise subsequent frames of visible-light image data and subsequent frames of fluorescent-light image data of at least one fluorophore;
wherein the image processor comprises:
a pattern recognition module configured to identify a vascular plexus structure in the visible-light image data and the fluorescent-light image data; and
an image blending module configured i) to assign at least one pseudo-color to at least one fluorophore and/or to the vascular plexus structure in the fluorescent-light image data to generate pseudo-color image data, and ii) to generate output image data including at least one of the visible-light image data, the pseudo-color image data, and any combination of the visible-light image data and the pseudo-color image data;
wherein the image output system is adapted to selectively and simultaneously output different output image data to the different output interfaces; and
wherein the image processor further comprises a kinetics analysis module configured to automatically identify a vascular plexus structure depending on a change of fluorescence intensity at a particular location over subsequent frames of the fluorescent-light image data, and to automatically assign to the vascular plexus structure a pseudo-color depending on a type of the vascular plexus structure to generate pseudo-color image data.

2. The augmented reality surgical microscope according to claim 1, wherein the fluorescent-light image data comprise at least two sets of fluorescent-band image data, each of the two sets representing a different fluorescence spectrum of at least one fluorophore.

3. The augmented reality surgical microscope according to claim 1, wherein the input image data comprise at least one of a three-dimensional atlas of pre-operative image data and ultrasound image data.

4. The augmented reality surgical microscope according to claim 1, wherein the fluorescent-light image data comprise at least two sets of fluorescent-band image data, wherein the input image data comprise at least one of a three-dimensional atlas of pre-operative image data and ultrasound image data, and wherein the image processor further comprises an elastic matching module configured to elastically match at least one of the fluorescent-light image data, at least one set of the fluorescence-band image data, the pseudo-color image data, the ultrasound image data, and the pre-operative image data to the visible-light image data.

5. The augmented reality surgical microscope according to claim 1, further comprising at least one of a multispectral camera and a hyperspectral camera for acquiring the fluorescent-light image data and the visible-light image data simultaneously in a plurality of spectral bands, wherein at least one spectral band of the at least one multispectral camera or hyperspectral camera matches a fluorescence band of the at least one fluorophore.

6. The augmented reality surgical microscope according to claim 1, wherein the pseudo-color image data comprise at least one of a time-varying pattern and a spatially varying pattern.

7. The augmented reality surgical microscope according to claim 1, further comprising a plurality of displays, wherein the image output system is adapted to output different output image data simultaneously to the plurality of displays.

8. A microscopy method for generating output image data of live tissue during surgery, the method comprising the steps of:
 acquiring input image data, the input image data comprising subsequent frames of visible-light image data and subsequent frames of fluorescent-light image data of at least one fluorophore;
 identifying at least one vascular plexus structure in at least one of the visible-light image data and the fluorescent-light image data;
 assigning a pseudo-color to at least one of the identified vascular plexus structure and/or to at least one fluorophore in the fluorescent-light image data to generate pseudo-color image data;
 generating output image data including at least one of the visible-light image data, the pseudo-color image data, and any combination of the visible-light image data with the pseudo-color image data; and
 simultaneously outputting different output image data;
 wherein a predetermined type of the vascular plexus structure is automatically identified in the input image data, the predetermined type of the vascular plexus structure including at least one of an arterial, venous, and capillary vascular plexus structure, and wherein the vascular plexus structure is automatically assigned a pseudo-color depending on the type of the vascular plexus structure.

9. The microscopy method according to claim 8, wherein the type of the vascular plexus structure is automatically identified depending on a variation of fluorescence in subsequent frames of the input image data.

10. The microscopy method according to claim 8, wherein a blood flow direction in the identified vascular plexus structure is automatically determined and marked by at least one pseudo-color in the output image data.

11. The microscopy method according to claim 8, wherein the fluorescent-light image data and the visible-light image data are acquired simultaneously in a plurality of spectral bands, wherein the live tissue contains more than one fluorophore, and wherein for each fluorophore in the live tissue having a different fluorescence emission spectrum, separate fluorescence-band image data are acquired as part of the fluorescent-light image data.

12. The microscopy method according to claim 8, wherein different fluorescence-band image data are provided for auto-fluorescence of the at least one fluorophore and for fluorescence directly triggered by illumination light generated by an illumination system.

13. A non-transitory computer readable medium storing a program causing a computer to execute the microscopy method according to claim 8.

* * * * *